(12) United States Patent
Damaj et al.

(10) Patent No.: US 8,962,595 B2
(45) Date of Patent: Feb. 24, 2015

(54) COMPOSITIONS OF SMALL MOLECULE THERAPEUTICS

(75) Inventors: Bassam B. Damaj, San Diego, CA (US); Richard Martin, San Diego, CA (US)

(73) Assignee: Nexmed Holdings, Inc., San Diego, CA (US)

(*) Notice: Subject to any disclaimer, the term of this patent is extended or adjusted under 35 U.S.C. 154(b) by 249 days.

(21) Appl. No.: 13/703,002

(22) PCT Filed: May 4, 2011

(86) PCT No.: PCT/US2011/000793
§ 371 (c)(1),
(2), (4) Date: Mar. 19, 2013

(87) PCT Pub. No.: WO2011/139373
PCT Pub. Date: Nov. 10, 2011

(65) Prior Publication Data
US 2013/0210766 A1 Aug. 15, 2013

Related U.S. Application Data

(60) Provisional application No. 61/343,781, filed on May 4, 2010.

(51) Int. Cl.
| | | |
|---|---|---|
| *A61K 31/7008* | (2006.01) | |
| *A61K 31/337* | (2006.01) | |
| *A61K 31/451* | (2006.01) | |
| *A61K 31/655* | (2006.01) | |
| *A61K 31/165* | (2006.01) | |
| *A61K 31/138* | (2006.01) | |
| *A61K 31/4439* | (2006.01) | |
| *A61K 31/445* | (2006.01) | |
| *A61K 31/635* | (2006.01) | |
| *A61K 31/341* | (2006.01) | |
| *A61K 31/549* | (2006.01) | |
| *A61K 9/00* | (2006.01) | |
| *A61K 47/10* | (2006.01) | |
| *A61K 47/14* | (2006.01) | |
| *A61K 47/18* | (2006.01) | |
| *A61K 9/48* | (2006.01) | |

(52) U.S. Cl.
CPC ........... *A61K 31/7008* (2013.01); *A61K 31/138* (2013.01); *A61K 31/337* (2013.01); *A61K 31/4439* (2013.01); *A61K 31/445* (2013.01); *A61K 31/635* (2013.01); *A61K 31/165* (2013.01); *A61K 31/341* (2013.01); *A61K 31/451* (2013.01); *A61K 31/549* (2013.01); *A61K 31/655* (2013.01); *A61K 9/0019* (2013.01); *A61K 47/10* (2013.01); *A61K 47/14* (2013.01); *A61K 47/18* (2013.01); *A61K 9/0095* (2013.01); *A61K 9/4858* (2013.01)
USPC .............................. 514/62; 514/150; 514/338

(58) Field of Classification Search
CPC .............. A61K 31/138; A61K 9/4858; A61K 31/4439; A61K 31/445; A61K 31/635; A61K 31/165
USPC ............................................ 514/62, 150, 338
See application file for complete search history.

(56) References Cited

U.S. PATENT DOCUMENTS

| | | | |
|---|---|---|---|
| 5,082,866 A | 1/1992 | Wong et al. | |
| 6,046,244 A * | 4/2000 | Buyuktimkin et al. | 514/785 |
| 6,414,028 B1 * | 7/2002 | Buyuktimkin et al. | 514/573 |
| 7,105,571 B2 * | 9/2006 | Yeager et al. | 514/573 |
| 2002/0065234 A1 | 5/2002 | Horwitz | |
| 2004/0146469 A1 | 7/2004 | Reed | |
| 2004/0185170 A1 | 9/2004 | Chungi et al. | |
| 2005/0004226 A1 | 1/2005 | Lu et al. | |
| 2006/0067898 A1 | 3/2006 | Kepka et al. | |
| 2007/0183936 A1 * | 8/2007 | Newsam et al. | 422/102 |
| 2007/0190019 A1 | 8/2007 | Guo et al. | |
| 2008/0318837 A1 | 12/2008 | Quay et al. | |
| 2008/0319370 A1 * | 12/2008 | Wolpert et al. | 604/20 |
| 2013/0178463 A1 * | 7/2013 | Damaj et al. | 514/211.07 |

FOREIGN PATENT DOCUMENTS

| | | |
|---|---|---|
| WO | WO 2005/000241 | 1/2005 |
| WO | WO 2008/045309 A1 | 4/2008 |
| WO | WO 2012/097160 A1 | 7/2012 |

OTHER PUBLICATIONS

Buyuktimkin et al., "Synthesis and Enhancing Effect of Dodecyl 2-(N,N-Dimethylamino)propionate on the Transepidermal Delivery of Indomethacin, Clonidine, and Hydrocortisone," Pharmaceutical Research, (1993), 10(11):1632-1637.
Davis et al. "Hollow Metal Microneedles for Insulin Delivery to Diabetic Rats," IEEE Transactions on Biomedical Engineering, (2005), 52:909-915.
Extended European Search Report dated Aug. 26, 2013 in related EP Patent Application No. 11777703.
Extended European Search Report dated May 12, 2014 in related EP Patent Application No. 11777706.
Varma et al., "Enhanced oral paclitaxel absorption with vitamin E-TPGS: Effect on solubility and permeability in vitro, in situ and in vivo," European Journal of Pharmaceutical Sciences, (2005), 25(4-5):445-453.
Wong, et al., "New Alkyl N,N-Dialkyl-Substituted amino acetates as transdermal penetration enhancers", Pharmaceutical Research, vol. 6, No. 4, pp. 286-295, (1989).

* cited by examiner

*Primary Examiner* — Brandon Fetterolf
*Assistant Examiner* — Yih-Horng Shiao
(74) *Attorney, Agent, or Firm* — Foley & Lardner LLP

(57) ABSTRACT

Compositions containing a small molecule therapeutic and an alkyl N,N-disubstituted amino acetate are disclosed. Inclusion of the alkyl N,N-disubstituted amino acetate enhances the pharmacokinetic properties of the small molecule therapeutic.

29 Claims, 4 Drawing Sheets

COMPOSITIONS OF SMALL MOLECULE THERAPEUTICS

CROSS-REFERENCE TO RELATED APPLICATION

This application claims the priority of U.S. Provisional Application Ser. No. 61/343,781, filed May 4, 2010, the disclosures of which are incorporated in their entirety herein by reference.

FIELD OF INVENTION

This invention relates to compositions of small molecule therapeutics with enhanced pharmacokinetic properties.

BACKGROUND OF INVENTION

Small molecule drug discovery is actively pursued by biotech companies to complement the therapeutic advances made with protein based drugs such as recombinant proteins and monoclonal antibodies. Moreover, small molecule drug treatments often may enjoy cost benefits. Patients are also more likely to accept orally available small molecule treatments than the typical injectable protein based drug. It has now been found that the pharmacokinetic properties of small molecule therapeutics can be improved by the co-administration of certain enhancers.

SUMMARY OF THE INVENTION

Pharmacokinetic properties of small molecule therapeutics such as the taxanes and small molecule drug substances classified according to the Biopharmaceutics Classification System (BCS) as Class 2-4 compounds are enhanced by the addition of an alkyl N,N-disubstituted-amino acetate in free base or salt form. A greater systemic exposure, higher peak plasma levels, and longer mean residence time can be achieved.

Particularly preferred are compositions comprising paclitaxel and dodecyl 2-(N,N-dimethylamino) propionate (DDAIP) in free base or salt form.

The solubility and absorption of small molecule drug substances classified as BCS 2 and BCS 4 compounds, are particularly enhanced by dodecyl 2-(N,N-dimethylamino) propionate in free base or salt form. Particularly preferred are the BCS Class 2 compounds, lansoprazole, haloperidol and sulfasalazine, the BCS Class 3 compounds, atenolol and glucosamine; and the BCS Class 4 compounds, furosemide and chlorothiazide.

Preferred routes of administration are oral and subcutaneous.

DETAILED DESCRIPTION OF PREFERRED EMBODIMENTS

As used herein, the term "small molecule therapeutic" denotes a low molecular weight organic compound which is not a polymer but binds with relatively high affinity to a biopolymer such as a protein, a nucleic acid, or polysaccharide and also alters the activity or function of the biopolymer. The upper molecular weight limit for a small molecule therapeutic is about 1000 Daltons which allows for diffusion across all membranes so that intracellular sites of action can be reached. Very small oligomers are also considered small molecules, e.g., dinucleotides, disaccharides, and the like. Illustrative are paclitaxel, DHA-paclitaxel, mesalamine (Pentasa®), motexafin gadolinium, temozolomide, erlotinib (Tarceva®), cinacalcet (Sensipar®), safinamide, simvastatin (Zocor®), pravastatin (Pravachol®), sildenafil, peptide mimetics, the siRNAs, and the like.

Taxanes are diterpenes utilized in cancer chemotherapy. Particularly well suited for purposes of the present invention are paclitaxel, docetaxel, tesetaxel, and mixture thereof.

Also suited for purposes of the present invention are small molecule therapeutic compounds that are potent and pharmaceutically relevant but usually poorly soluble or insoluble compounds. A Biopharmaceutics Classification System (BCS) is a guide provided by the U.S. Food and Drug Administration for predicting the intestinal drug absorption. The system correlates in vitro drug product dissolution and in vivo bioavailability based on recognition that drug dissolution and gastrointestinal permeability are fundamental parameters controlling rate and extent of drug absorption. Four drug classes are defined in an article by Amidon G. L, et al., "*A theoretical basis for a biopharmaceutic drug classification: the correlation of in vitro product dissolution and in vivo bioavailability.*" Pharm. Res., 12(3), 413-20 (1995).

According to the Biopharmaceutics Classification System, drug substances are classified as follows:

Class 1—High permeability, High solubility drugs. Those compounds are well absorbed and their absorption rate is usually higher than excretion. An example compound is metoprolol.

Class 2—High permeability, Low solubility drugs. The bioavailability of those products is limited by their solvation rate. A correlation between the in vivo bioavailability and the in vitro solvation can be found. Example compounds are lansoprazole, haloperidol, sulfasalazine, and glibenclamide.

Class 3—Low permeability, High solubility drugs. The absorption is limited by the permeation rate but the drug is solvated very fast. Example compounds are atenolol, glucosamine (or salts thereof), and cimetidine.

Class 4—Low permeability, Low solubility drugs. Those compounds have a poor bioavailability. Usually they are not well absorbed over the intestinal mucosa and a high variability is expected. Example compounds are furosemide, chlorothiazide, and hydrochlorothiazide.

The drugs are classified in BCS on the basis of the following parameters: 1. solubility; 2. permeability; and 3. dissolution. The class boundaries for solubility are based on the highest dose strength of an immediate release product. A drug is considered highly soluble when the highest dose strength is soluble in 250 milliliters (ml) or less of aqueous media over the pH range of 1 to 7.5. The class boundaries for permeability are based indirectly on the extent of absorption of a drug substance in humans and directly on the measurement of rates of mass transfer across human intestinal membrane. Alternative non-human systems capable of predicting the drug absorption in humans can be used (such as in vitro culture methods). A drug substance is considered highly permeable when the extent of absorption in humans is determined to be 90% or more of the administered dose based on a mass-balance determination or in comparison to an intravenous dose. The class boundaries for dissolution for an immediate release product to be considered rapidly dissolving is when no less than 85% of the labeled amount of the drug substance dissolves within 30 minutes using a USP Dissolution Apparatus 1 at 100 RPM or Apparatus 2 at 50 RPM in a volume of 900 ml or less in a media of 0.1N HCl or simulated gastric fluid or pH 4.5 buffer and pH 6.8 buffer or simulated intestinal fluid.

Class 2-4 compounds are particularly well suited for compositions embodying this invention. Preferred are small molecule therapeutic compounds appearing in the *WHO List of Essential Drugs*, 16th Ed., revised March 2010. Particularly preferred small molecule therapeutic compounds are lansoprazole, haloperidol, and sulfasalazine in Class 2; atenolol, and glucosamine in Class 3; and furosemide and chlorothiazide in Class 4.

The alkyl N,N-disubstituted amino acetates suitable for purposes of the present invention are represented by the formula:

wherein n is an integer having a value in the range of about 4 to about 18; R is a member of the group consisting of hydrogen, $C_1$ to $C_7$ alkyl, benzyl and phenyl; $R_1$ and $R_2$ are members of the group consisting of hydrogen and $C_1$ to $C_2$ alkyl; $R_3$ and $R_4$ are members of the group consisting of hydrogen, methyl and ethyl.

Preferred alkyl(N,N-disubstituted amino)-acetates are $C_4$ to $C_{18}$ alkyl(N,N-disubstituted amino)-acetates and $C_4$ to $C_{18}$ alkyl(N,N-disubstituted amino)-propionates as well as pharmaceutically acceptable salts and derivatives thereof. Exemplary specific alkyl-2-(N,N-disubstituted amino)-acetates include Alkyl-2-(N,N-disubstituted amino) acetates are known. For example, dodecyl 2-(N,N-dimethylamino)-propionate (DDAIP) is available from Steroids, Ltd. (Chicago, Ill.). In addition, alkyl-2-(N,N-disubstituted amino) alkanoates can be synthesized from more readily available compounds as described in U.S. Pat. No. 4,980,378 to Wong et al., which is incorporated herein by reference to the extent that it is not inconsistent. As described therein, alkyl-2-(N,N-disubstituted amino) acetates are readily prepared via a two-step synthesis. In the first step, long chain alkyl chloroacetates are prepared by reaction of the corresponding long chain alkanols with chloromethyl chloroformate or the like in the presence of an appropriate base such as triethylamine, typically in suitable solvent such as chloroform. The reaction can be depicted as follows:

wherein n, R, $R_1$, $R_2$, $R_3$ and $R_4$ are defined as above. The reaction temperature may be selected from about 10 degrees Celsius to about 200 degrees Celsius or reflux, with room temperature being preferred. The use of a solvent is optional. If a solvent is used, a wide variety of organic solvents may be selected. Choice of a base is likewise not critical. Preferred bases include tertiary amines such as triethylamine, pyridine and the like. Reaction time generally extends from about one hour to three days.

In the second step, the long chain alkyl haloacetate such as chloroacetate is condensed with an appropriate amine according to the scheme:

wherein n, R, $R_1$, $R_2$, $R_3$ and $R_4$ are defined as before. Excess amine reactant is typically used as the base and the reaction is conveniently conducted in a suitable solvent such as ether. This second step is preferably run at room temperature, although temperature may vary. Reaction time usually varies from about one hour to several days. Conventional purification techniques can be applied to ready the resulting ester for use in a pharmaceutical composition.

The free base forms of the foregoing compounds are liquids at ambient temperature. The salt forms, on the other hand, are solids. For administration to a patient, both forms can be combined with the small molecule therapeutic in a physiologically acceptable carrier such as water or water-solvent admixture depending upon the solubility of the small molecule therapeutic. A pharmacologically acceptable carrier for the active ingredient and the alkyl N,N-disubstituted amino acetate can be a liquid or a solid. The choice of the particular carrier is dictated usually by the active ingredient. The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting the active ingredient from one, organ, or portion of the body, to another organ, or portion of the body. Each carrier must be "acceptable" in the sense of being compatible with the active ingredient and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pryogen-free water; (17) isotonic saline; (18) Ringer's solution; (19) ethyl alcohol; (20) phosphate buffer solutions; and (21) other non-toxic compatible substances employed in pharmaceutical formulations.

An illustrative water-solvent carrier for taxanes that is physiologically acceptable is a water-polyethylene glycol (PEG) admixture containing about 10 to about 20 percent (v/v) polyethylene glycol 300 (PEG 300) or polyethylene glycol 400 (PEG 400).

The amount of taxane administered to a patient can vary, but usually is in the range of about 200 to 250 mg/m$^2$. In one embodiment, paclitaxel (Taxol®) was formulated in either 10% polyethylene glycol 400 (PEG 400) in water, or in aqueous solutions of DDAIP, or its hydrochloric salt, DDAIP.HCL (40%).

Example I

Using Sprague Dawley rats as an animal model, the body weights of the animals were measured prior to dosing to determine the appropriate amount of test article to deliver. Animals were dosed (5 mg/kg) by oral gavage (PO) or subcutaneously (SC) with the test composition in the different formulations as a single bolus. Then blood samples were taken via the lateral tail vein at 0.5, 1, 2, 4, 8 and 24 hours following the dose.

Blood samples were collected into blood collection tubes containing Na$_2$EDTA, placed on ice and within 30 minutes of sampling the blood samples were centrifuged to obtain plasma. The plasma was separated from the cellular component and placed in microcentrifuge tubes and frozen, then stored at −80° C. until processed for analysis by LC-MS/MS (liquid chromatography-mass spectrometry with peptide mass fingerprinting). Standard samples were created by adding known amounts of paclitaxel to blank rat plasma. Standard curves were created by analyzing the standard samples by LC-MS/MS and using the resultant areas under the chromatographic peaks in conjunction with the known concentration of the samples.

The experimental samples were analyzed using the same method and the areas under the chromatographic peaks were used in conjunction with the standard curves to calculate the concentration of paclitaxel in the samples. The peak plasma concentrations ($C_{max}$) of paclitaxel were increased 10-fold after oral dosing and 2-fold after subcutaneous dosing in DDAIP.HCL formulation as compared to the PEG formulation. Use of the DDAIP.HCL formulation resulted in longer absorption phases and later onset of $T_{max}$ times when dosed both orally and subcutaneously compared to the use of the PEG formulation.

Figure 1:
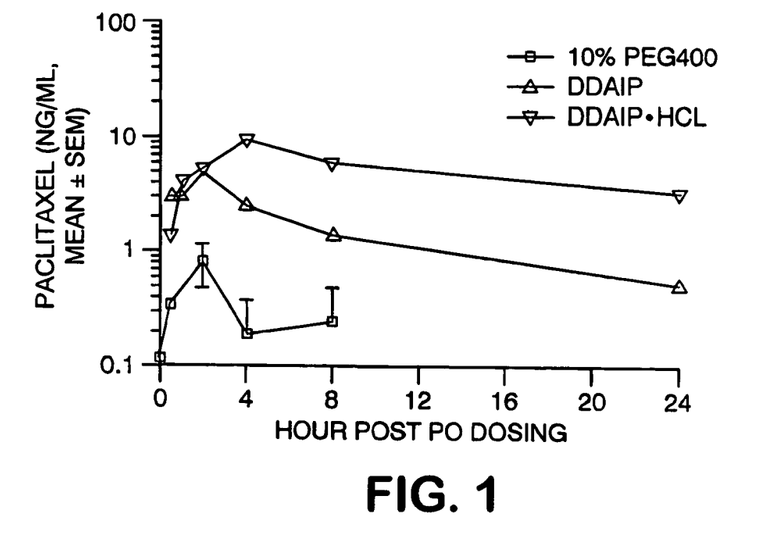
FIG. 1 is a graphical representation of paclitaxel concentrations in rat plasma samples after oral (PO) dosing (5 mg/kg); data points represent mean values and error bars represent standard errors of the mean values.
Figure 2:
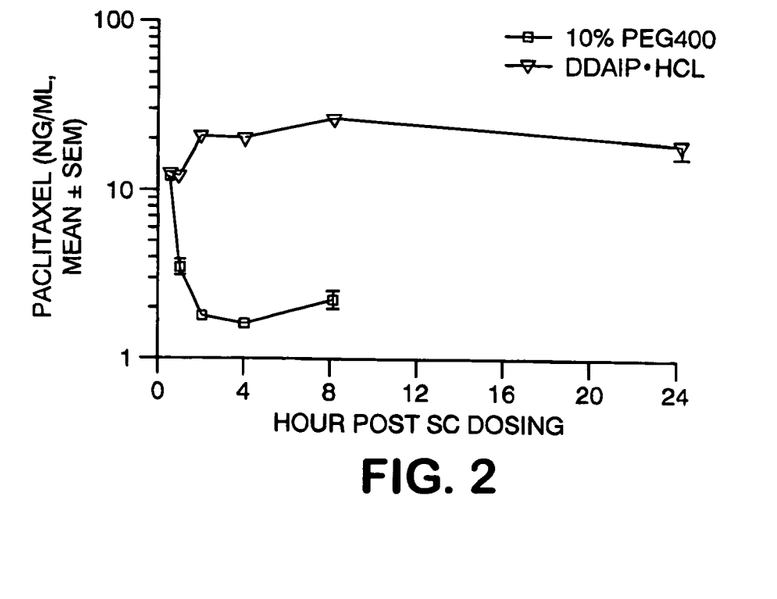
FIG. 2 is a graphical representation of paclitaxel concentrations in rat plasma samples after subcutaneous (SC) dosing (5 mg/kg); data points represent mean values and error bars represent standard errors of the mean values.

The overall systemic exposure (AUC) and bioequivalence were increased with the DDAIP.HCL formulation as compared to when the PEG 400 formulation was used. After oral administration with the DDAIP.HCL formulation, the overall systemic exposure of paclitaxel was increased approximately 75 times and after subcutaneous dosing approximately 20 times compared to the PEG formulations via the same administration routes. The mean residence time (MRT) increased to 9.8 hours after oral dosing and 11.5 hours after subcutaneous dosing when the DDAIP.HCL formulation was used compared to the PEG 400 formulation (3.8 hours PO and 8.5 hours SC). Additionally, dosing with DDAIP.HCL, the hydrochloride salt of DDAIP, resulted in greater systemic exposure, higher peak plasma levels and longer MRT compared to DDAIP alone. The experimental results are graphically presented in FIGS. 1 and 2.

It can be concluded from these results that the formulation DDAIP.HCL provides superior pharmacokinetic properties to paclitaxel compared to the polyethylene glycol (PEG 400) formulation. Additionally, the DDAIP.HCL formulation provided superior pharmacokinetic properties to paclitaxel compared to DDAIP alone.

Standard samples for PO delivery of paclitaxel (Taxol®) formulated in 10% PEG 400, DDAIP and 40% DDAIP.HCL were created by adding known amounts of paclitaxel to blank rat plasma. The Standard samples were analyzed by LC-MC/MS and the resultant areas under the chromatographic peaks were used to construct a standard curve. The results are shown in Tables I-III for the PO delivery.

TABLE I

Results of the LC-MS/MS Analysis of the Standard Samples.

| Actual Conc. | Mean Area Ratio | First Injection | Second Injection | Mean Measured Conc. | Accuracy |
|---|---|---|---|---|---|
| 0.5 | 0.00365 | 0.55 | 0.448 | 0.449 | 99.80 |
| 1 | 0.0061 | 1.045 | 1.274 | 1.1595 | 115.95 |
| 5 | 0.0215 | 4.475 | 4.565 | 4.52 | 90.40 |
| 10 | 0.0454 | 9.915 | 9.876 | 9.8955 | 98.96 |
| 25 | 0.1144 | 24.346 | 26.561 | 25.4535 | 101.81 |
| 50 | 0.2218 | 47.726 | 51.603 | 49.6645 | 99.33 |
| 75 | 0.33305 | 70.706 | 78.75 | 74.728 | 99.64 |
| 100 | 0.4797 | 102.494 | 113.091 | 107.7925 | 107.79 |

The best fit straight line by least squares linear regression is represented by the formula:

Area Ratio=4.66$E$-3(conc'n in ng/ml)−2.19$E$-03

$R^2$=9.97$E$-01

TABLE II

Results of the LC-MS/MS Analysis of the PO Samples.

| Formula | Time (Hr.) | R-1 | R-2 | Mean | SEM |
|---|---|---|---|---|---|
| 10% PEG400 | 0 | 0.232 | 0 | 0.1 | 0.1 |
| | 0.5 | 0.325 | 0.351 | 0.3 | 0.0 |
| | 1 | 0.48 | 0 | 0.0 | 0.0 |
| | 2 | 0 | 1.137 | 0.8 | 0.3 |
| | 4 | 0 | 0.369 | 0.2 | 0.2 |
| | 8 | 0 | 0.481 | 0.2 | 0.2 |
| | 24 | 0 | 0 | 0.0 | 0.0 |

TABLE II-continued

Results of the LC-MS/MS Analysis of the PO Samples.

| Formula | Time (Hr.) | R-1 | R-2 | Mean | SEM |
|---|---|---|---|---|---|
| DDAIP | 0 | 0 | 0 | 0.0 | 0.0 |
| | 0.5 | 2.963 | 3.215 | 3.1 | 0.1 |
| | 1 | 3.32 | 3.092 | 3.2 | 0.1 |
| | 2 | 4.539 | 5.306 | 4.9 | 0.4 |
| | 4 | 2.679 | 2.376 | 2.5 | 0.2 |
| | 8 | 1.459 | 1.331 | 1.4 | 0.1 |
| | 24 | 0.487 | 0.556 | 0.5 | 0.0 |
| 40% DDAIP HCl | 0 | 0 | 0 | 0.0 | 0.0 |
| | 0.5 | 1.401 | 1.159 | 1.3 | 0.1 |
| | 1 | 4.168 | 3.652 | 3.9 | 0.3 |
| | 2 | 5.169 | 4.872 | 5.0 | 0.1 |
| | 4 | 9.699 | 8.008 | 8.9 | 0.8 |
| | 8 | 6.009 | 5.124 | 5.6 | 0.4 |
| | 24 | 3.012 | 3.057 | 3.0 | 0.0 |

TABLE III

Derivation of Pharmacokinetic Parameters from the PO Data.

| Formulation | Parameter (units) | R-1 | R-2 | Mean | SEM |
|---|---|---|---|---|---|
| 10% PEG400 | $C_{max}$ (ng/mL) | 0.5 | 1.1 | 0.8 | 0.46 |
| | $T_{max}$ (hr.) | 2 | 2 | 2.0 | 0.00 |
| | AUC (ng* hr/mL) | 0.9 | 7.8 | 4.4 | 4.85 |
| | Mean Residence Time (MRT, hr.) | 1.6 | 6.0 | 3.8 | 3.06 |
| | $T_{1/2\,MRT}$ (hr.) | 1.1 | 4.1 | 2.6 | 2.12 |
| DDAIP | $C_{max}$ (ng/mL) | 4.5 | 5.3 | 4.9 | 0.54 |
| | $T_{max}$ (hr.) | 2 | 2 | 2.0 | 0.00 |
| | AUC (ng* hr/mL) | 37.3 | 36.8 | 37.0 | 0.38 |
| | Mean Residence Time (MRT, hr.) | 6.9 | 7.1 | 7.0 | 0.10 |
| | $T_{1/2\,MRT}$ (hr.) | 4.8 | 4.9 | 4.9 | 0.07 |
| 40% DDAIP HCl | $C_{max}$ (ng/mL) | 9.7 | 8.0 | 8.9 | 1.20 |
| | $T_{max}$ (hr.) | 4 | 4 | 4.0 | 0.00 |
| | AUC (ng* hr/mL) | 124.9 | 110.3 | 117.6 | 10.26 |
| | Mean Residence Time (MRT, hr.) | 9.6 | 10.1 | 9.8 | 0.35 |
| | $T_{1/2\,MRT}$ (hr.) | 6.6 | 7.0 | 6.8 | 0.24 |
| Bioequivalence ($AUC_{DDAIP}/AUC_{10\%\,PEG}$) | | | | 39.7 | 4.7 | 22.2 | 24.71 |
| Bioequivalence ($AUC_{40\%\,DDAIP\text{-}HCl}/AUC_{10\%\,PEG}$) | | | | 132.8 | 41.2 | 73.5 | 83.87 |

$T_{1/2}$ MRT = 0.693 * MRT

Standard samples for SC delivery of paclitaxel formulated in 10% PEG 400 and 40% DDAIP.HCL were created by adding known amounts of paclitaxel to blank rat plasma. The Standard samples were analyzed by LC-MS/MS, and the resultant areas under the chromatographic peaks were used to construct a standard curve. and in Table IV and VI for the SC delivery.

TABLE IV

Results of the LC-MS/MS analysis of the Standard Samples.

| Actual Conc. | Mean Area Ratio | First Injection | Second Injection | Mean Measured Conc. | Accuracy |
|---|---|---|---|---|---|
| 0.2 | 0.0008 | N/A | 0.211 | 0.211 | 105.50 |
| 0.5 | 0.00135 | 0.426 | 0.463 | 0.4445 | 88.90 |
| 1 | 0.00285 | 1.063 | 1.114 | 1.0885 | 108.85 |
| 5 | 0.01185 | 4.876 | 5.066 | 4.971 | 99.42 |
| 10 | 0.02335 | 9.705 | 10.103 | 9.904 | 99.04 |
| 25 | 0.0617 | 26.224 | 26.661 | 26.4425 | 105.77 |
| 50 | 0.1092 | 46.623 | 47.127 | 46.875 | 93.75 |
| 75 | 0.1765 | 75.029 | 76.672 | 75.8505 | 101.13 |
| 100 | 0.2335 | 101.111 | 99.734 | 100.4225 | 100.42 |

The best fit straight line by least squares linear regression is represented by the formula:

Area Ratio=2.32$E$-03 (conc'n in ng/ml)+1.98$E$-04

$R^2$=9.99$E$-01

TABLE V

Results of the LC-MS/MS Analysis of the Experimental SC Samples.

| Formula | Time (Hr.) | R-1 | R-2 | R-3 | Mean | SEM |
|---|---|---|---|---|---|---|
| 10% PEG 400 | 0 | 0 | 0 | 0 | 0.0 | 0.0 |
| | 0.5 | 10.913 | 12.249 | 12.774 | 11.6 | 0.7 |
| | 1 | 3.167 | 3.094 | 4.223 | 3.1 | 0.0 |
| | 2 | 1.667 | 1.829 | 1.942 | 1.7 | 0.1 |
| | 4 | 1.617 | 1.667 | 1.578 | 1.6 | 0.0 |
| | 8 | 2.763 | 1.882 | 2.062 | 2.3 | 0.4 |
| | 24 | 0.755 | 1.175 | 0.906 | 1.0 | 0.2 |
| DDAIP | 0 | 0 | 0 | 0 | 0.0 | 0.0 |
| | 0.5 | 13.017 | 11.983 | 10.804 | 12.5 | 0.5 |
| | 1 | 12.399 | 10.938 | 11.891 | 11.7 | 0.7 |
| | 2 | 17.564 | 22.256 | 20.427 | 19.9 | 2.3 |
| | 4 | 17.55 | 19.542 | 20.66 | 18.5 | 1.0 |
| | 8 | 23.776 | 25.873 | 25.143 | 24.8 | 1.0 |
| | 24 | 15.818 | 14.976 | 21.433 | 15.4 | 0.4 |

TABLE VI

Derivation of Pharmacokinetic Parameters from the SC Data

| Formulation | Parameter (units) | R-1 | R-2 | R-3 | Mean | SEM |
|---|---|---|---|---|---|---|
| 10% PEG 400 | $C_{max}$ (ng/mL) | 10.9 | 12.2 | 12.8 | 12.0 | 0.68 |
| | $T_{max}$ (hr.) | 0.5 | 0.5 | 0.5 | 0.5 | 0.00 |
| | AUC (ng * hr/mL) | 48.9 | 44.4 | 45.1 | 46.1 | 1.70 |
| | Mean Residence Time (MRT, hr.) | 8.1 | 9.2 | 8.2 | 8.5 | 0.42 |
| | $T_{1/2\,MRT}$ (hr.) | 5.6 | 6.4 | 5.7 | 5.9 | 0.29 |
| 40% DDAIP HCl | $C_{max}$ (ng/mL) | 23.8 | 25.9 | 25.1 | 24.9 | 0.75 |
| | $T_{max}$ (hr.) | 8 | 8 | 8 | 8.0 | 0.00 |
| | AUC (ng * hr/mL) | 459.1 | 484.7 | 529.8 | 491.2 | 25.32 |
| | Mean Residence Time (MRT, hr.) | 11.4 | 10.8 | 12.2 | 11.5 | 0.47 |
| | $T_{1/2\,MRT}$ (hr.) | 7.9 | 7.5 | 8.4 | 7.9 | 0.33 |
| Bioequivalence ($AUC_{40\%\,DDAIP\text{-}HCl}/AUC_{20\%\,PEG}$) | | 9.4 | 10.9 | 11.8 | 10.7 | 0.85 |

$T_{1/2\,MRT}$ = 0.693 * MRT

Figure 3:
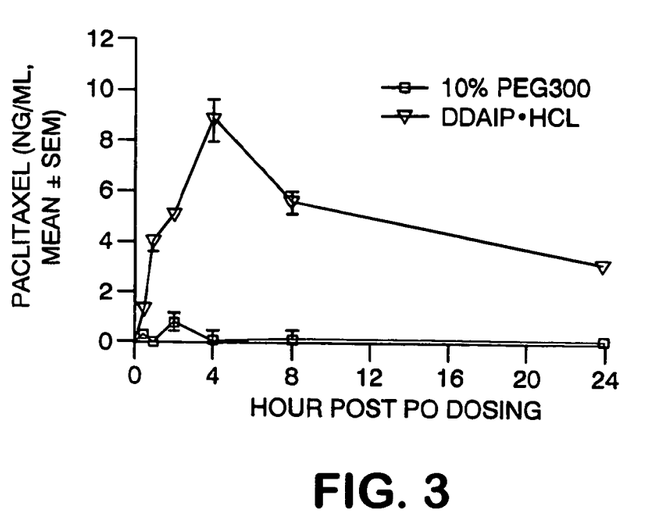
FIG. 3 is another graphical representation of paclitaxel concentrations in rat plasma samples after oral (PO) dosing (5 mg/kg); data points represent mean values and error bars represent standard errors of the mean values.

In another embodiment, paclitaxel (Taxol®) was formulated in either 10% polyethylene glycol 300 (PEG 300) in water, or in aqueous solution of DDAIP.HCL (40%). Rats were dosed (5 mg/kg) by oral gavage (PO), as above, with the test composition in the different formulations as a single bolus and blood plasma levels were determined. A 30-fold increase in AUC was achieved with the aqueous solution of DDAIP.HCL over that achieved with the PEG 300 formulation, with no inhibition of P-glycoprotein (P-gp) up to 10 mM. The results are graphically represented in FIG. 3.

Example II

Two small molecule therapeutic compounds were selected from each of BCS Class 2, BCS Class 3, and BCS Class 4 for oral delivery (PO) to jugular vein cannulated (JVC) male Sprague Dawley rats (200-250 gram weight). The BCS Class 2 compounds were haloperidol and sulfasalazine. Haloperidol is an antipsychotic butyrophenone sold under the brand name Haldol® and sufasalazine is an anti-inflammatory sulfa drug derivative of mesalazine sold under the brand name Azulfidine®. The BCS Class 3 compounds were atenolol, and glucosamine (in the salt form glucosamine sulfate). Atenolol is in the class of beta blocker drugs and is sold under the brand names Sensormin® and Tenomin®. The BCS Class 4 compounds were furosemide (Lasix®) and chlorothiazide)(Diuril®), both of which are diuretics.

The compounds from BCS Class 2, 3 and 4 were each formulated at 5 mg/ml in a liquid carrier of either an aqueous solution of polyethylene glycol 400 (20% PEG 400), or an aqueous solution of DDAIP.HCL (20%). The BCS Class 2 compounds, haloperidol and sulfasalazine, formed suspensions in either liquid vehicle. The BCS Class 3 compounds, atenolol and glucosamine sulfate formed suspensions in the PEG 400 vehicle and solutions in the water vehicle. The BCS Class 4 compounds, furosemide and chlorothiazide formed suspensions in the PEG400 vehicle and solutions in the water vehicle.

Cohorts of three animals per group were placed in the study. On day 1, animals from each group were dosed at 30 mg/kg (6 ml/kg) by oral gavage (PO). Animals were fed at the time of dosing. Serial blood samples were collected at pre-dose, and after post-dose intervals of 30 minutes, 1 hour, 2 hours and 4 hours. The blood samples were collected into lithium heparin-coated tubes. At each time point, 0.15 ml of blood was collected via left jugular vein cannulae and processed for collection of plasma by centrifuging at approximately 2,000 rpm for approximately 10 minutes. The cellular fraction of the blood was discarded. Collection times and volume of plasma samples were recorded and tabulated. Plasma samples were transferred into clean tubes and snap frozen onto dry ice. Samples were stored at −80° C. until ready for bio-analysis by LC/MS/MS. The results are tabulated in Table VII. The drug concentration was measured from supernatant after centrifugation of the dosing solution difficult-to-absorb small molecule therapeutic compounds by improving their solubility and, hence, their absorption.

Example III

Male CD1 mice were used (Harlan, USA) in this study and weighed 20-24 grams at the time of use. A 1.5% aqueous methylcellulose solution was made overnight with continuous heating and stirring. To this, 50 mg Phenol Red was added to 100 ml of 1.5% aqueous methylcellulose. Mice were pre-treated with saline or 20% DDAIP free base (5 ml/kg) with and without lansoprazole (10 mg/kg) 15 minutes before challenge with Phenol Red at $T_0$ (150 μl/mouse). Ten and thirty minutes after Phenol Red challenge, mice were euthanized with isoflurane and the stomachs rapidly excised (clamping the pyloric and cardiac sphincters to avoid loss of contents). Stomachs were then cut into several pieces and placed in 15 ml tubes containing 2 ml water prior to processing for $A_{558}$ nm measurements. Several mice were sacrificed immediately after gavage with dye to act as an indicator of maximum dye retrieval (75 μg dye was dosed to each mouse).

Figure 4:
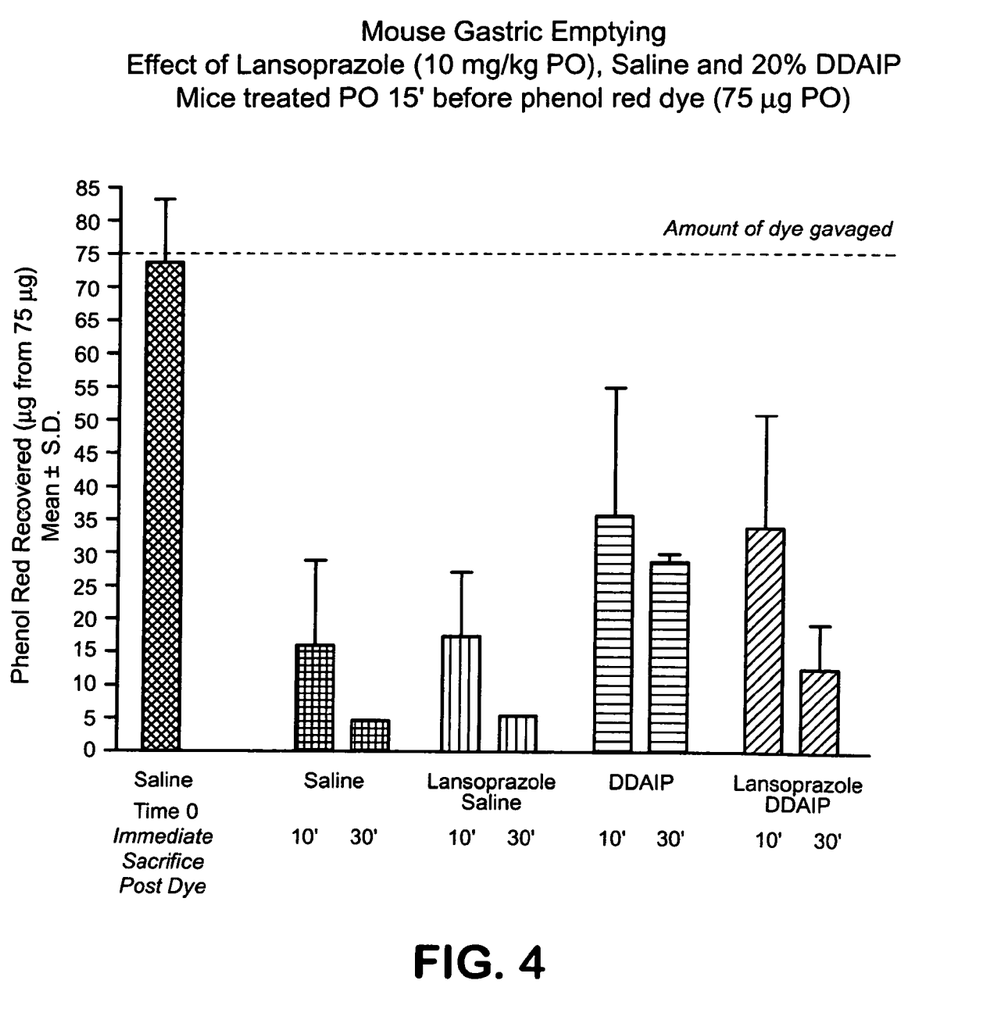
FIG. 4 is a graphical representation of lansoprazole and DDAIP effects on gastric emptying in mice.

Data (n=3) for stomach emptying (i.e., the amount of dye remaining in the stomach) 10 and 30 minutes after challenge are shown in FIG. 4. Pre-treatment with DDAIP slowed stomach emptying compared to pre-treatment with saline at both time points. The same pattern was observed when lansoprazole was administered in either vehicle. Mice that were challenged with dye and immediately sacrificed had stomachs that contained virtually all the administered amount of dye (75 μg). This experiment shows that increased absorption is not due to faster gastric emptying so that, in addition to

TABLE VII

Oral Formulations - Solubility and AUC

| BCSCI | Compound 5 mg/ml | Aqueous Dosing solution (20%) | Drug Conc. mg/ml | Sol.* over PEG | AUC 0-24 h** | Sol.*** $H_2O$ mg/ml | Sol. Over $H_2O$ |
|---|---|---|---|---|---|---|---|
| 2 | Haloperidol | PEG 400 | 1.43 | — | 1.3 | 0.001 | 1430 |
|   |             | DDAIP•HCL | 1.73 |   |     |       | 1730 |
| 2 | Sulfasalazine | PEG400 | <0.01 | >446 | 24 | 0.010 | 0 |
|   |             | DDAIP•HCL | 4.46 |   |     |       | 446 |
| 3 | Glucosamine | PEG 400 | 4.52 | — | 2.5 | 551.000 | — |
|   |             | DDAIP•HCL | 4.42 |   |     |       | — |
| 3 | Atenolol | PEG 400 | 2.74 | 2.300 | 2.1 | 13.500 | — |
|   |             | DDAIP•HCL | 6.28 |   |     |       | — |
| 4 | Furosemide | PEG 400 | <0.01 | >400 | 9.1 | 0.006 | 0 |
|   |             | DDAIP•HCL | 4.00 |   |     |       | 667 |
| 4 | Chlorothiazide | PEG 400 | <0.01 | >363 | 18 | 3 | 0 |
|   |             | DDAIP•HCL | 3.63 |   |     |       | 12 |

Notes to Table VII.
*Solubility improvement fold over PEG 400
**AUC-improvement fold for hourly period
***Reported solubility from the literature
****Solubility improvement fold over water.
*****Pharmacokinetic parameters were calculated with PK Solutions 2.0 software (Summit Research Services, Montrose, CO)

The results show that the DDAIP.HCL improves the solubility of the compounds when compared to water or PEG vehicle. This improvement is also reflected in the enhanced blood levels of drug in the rat plasma. In particular, the Class 2 and 4 compounds, where solubility is a determining factor, displayed over a 400-fold solubility improvement and over a 20-fold AUC improvement. The data show that formulations with DDAIP.HCL significantly improve the oral delivery of improvement in solubility, protection of API in stomach and/or increased absorption in the stomach and intestine are other likely mechanisms.

Example IV

A total of nine male Beagle dogs (three groups of n=3 with body weights ranging from 9.4-10.6 kg) were used from Bio-Quant's colony (originally sourced from Marshall Farms, North Rose, N.Y., USA) and fasted overnight prior to an intramuscular injection of pentagastrin (6 μg/kg at 0.03 ml/kg) one hour before treatment with lansoprazole (15 mg per animal). Pre-treatment blood samples were taken prior to intramuscular injection with pentagastrin (−60 minutes) and treatment with lansoprazole (time 0). Dogs were then treated with lansoprazole as detailed in Table VIII below.

TABLE VIII

Experimental Grouping Table

| Group (n = 3) | Pre-Treatment | Dose | Route | Regimen | Bleeds | Overnight Fasting |
|---|---|---|---|---|---|---|
| 1, 2.3 | Pentagastrin | 60 μg/kg at 0.03 ml/kg | I.M. | Single (−60') | Predose (−60') | Yes |

| | Treatment | Dose per Dog | Route | Regimen | Bleeds | Overnight Fasting |
|---|---|---|---|---|---|---|
| 1 | Lansoprazole powder in 1 gelatin capsule | 15 mg | Oral gavage with Petfiller followed by 50 ml H$_2$O | 1 capsule per dog | Pre-dose, 30 min, 1 hr, 2 hr. 4 hr, 8 hr, 24 hr. post-dosing | Yes |
| 2 | Lansoprazole powder in 1 gelatin capsule containing 0.625 g of 100% DDAIP•base | 15 mg | | 1 capsule per dog | | |
| 3 | Lansoprazole powder in 5 gelatin capsules, each containing 0.625 g of 100% DDAIP•base | 15 mg | | 5 capsules per dog | | |

Formulations:

Group 1: Dosed with 15 mg lansoprazole powder in a single gelatin capsule (size 00).

Group 2: 700 μl (0.625 g) DDAIP.base was mixed with 15 mg of lansoprazole powder in a single gelatin capsule (size 00).

Group 3: 700 μl (0.625 g) DDAIP.base was mixed with 3 mg of lansoprazole powder in each of 5 gelatin capsules (size 00).

Blood Collection:

At each time point shown in Table VIII above, 0.5 ml whole blood samples were collected from the saphenous vein into heparinized blood collection tubes. Following centrifugation at 10,000 rpm at 4° C. for 10 minutes, plasma samples were collected and stored at −80° C. until analysis by LCMS-MS.

RESULTS AND CONCLUSION

Figure 5:
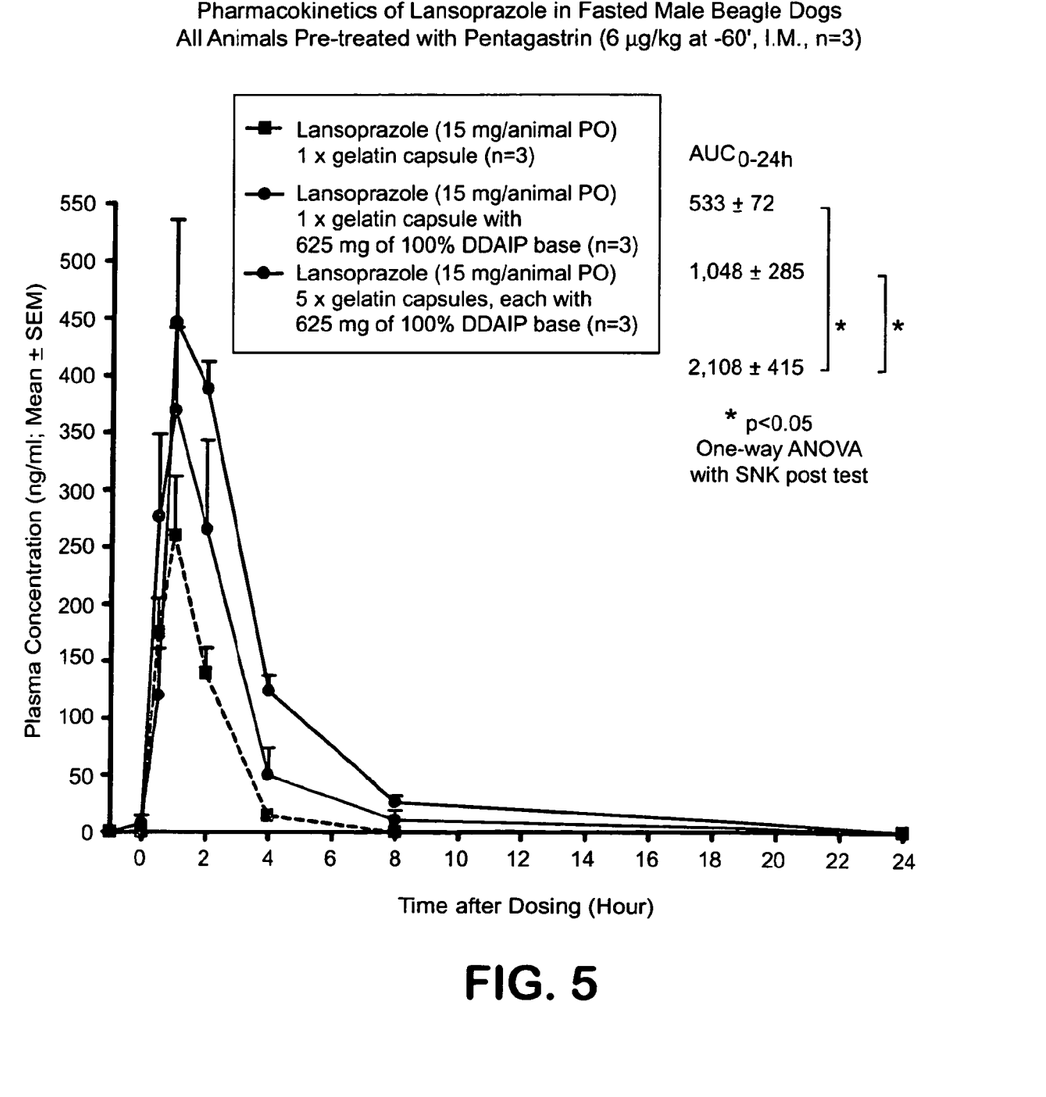
FIG. 5 is a graphical representation of pharmacokinetic profile of lansoprazole in dog plasma samples after oral administration with and without DDAIP.

FIG. 5 shows the pharmacokinetic profiles after oral treatment with lansoprazole in all groups. Table IX details individual parameters, such as $T_{max}$, $C_{max}$ and $T\frac{1}{2}$. In comparison to treatment with lansoprazole powder alone, the addition of DDAIP (0.625 g in 12 capsule or 3.125 g in a total of capsules) resulted in higher $C_{max}$, longer $T\frac{1}{2}$ (Table IX) and significantly increased AUC values. $T_{max}$ occurred at 1 hour in all groups. Furthermore, AUC values were also significantly different in both DDAIP-treated groups.

This study illustrates that the pharmacokinetic profile of orally-administered lansoprazole is significantly improved in dogs by the addition of DDAIP to the formulation. In addition, the group treated with 3.125 g DDAIP in five gelatin capsules exhibited significantly improved pharmacokinetic properties when compared to groups treated with control formulation or 0.625 g DDAIP in one gelatin capsule. These improvements are representative of human subjects' dosing since this experiment was performed at physiological pH of the human stomach.

TABLE IX

Pharmacokinetic Properties in all Groups

| Group | $C_{max}$ (ng/ml) | $T_{max}$ (hr.) | $T\frac{1}{2}$ (hr.) |
|---|---|---|---|
| 1 | 260 | 1 | 0.61 |
| 2 | 369 | | 1.78 |
| 3 | 445 | | 1.78 |

The foregoing discussion and the examples are illustrative, but are not to be taken as limiting. Still other variants within the spirit and scope of this invention are possible and will readily present themselves to those skilled in the art.

The invention claimed is:

1. An oral or subcutaneously injectable composition consisting of a small molecule therapeutic, an alkyl N,N-disubstituted-amino acetate, and one or more pharmaceutically acceptable carriers.

2. The composition in accordance with claim 1 wherein the small molecule therapeutic is selected from the group consisting of a taxane, and a compound classified under the Biopharmaceutics Classification System (BCS) in at least one of Class 2, Class 3 or Class 4.

3. The composition in accordance with claim 2 wherein the taxane is a member of the group consisting of paclitaxel, docetaxel, tesetaxel, and mixtures thereof.

4. The composition in accordance with claim 2 wherein the compound is a member of BCS Class 2.

5. The composition in accordance with claim 4 wherein the compound is selected from the group consisting of lansoprazole, haloperidol, sulfasalazine, and glibenclamide.

6. The composition in accordance with claim 2 wherein the compound is a member of BCS Class 3.

7. The composition in accordance with claim 6 wherein the compound is selected from the group consisting of atenolol, glucosamine or salt thereof, and cimetidine.

8. The composition in accordance with claim 2 wherein the compound is a member of BCS Class 4.

9. The composition in accordance with claim 8 wherein the compound is selected from the group consisting of furosemide, chlorothiazide, and hydrochlorothiazide.

10. The composition in accordance with claim 1 wherein the alkyl N,N-disubstituted-amino acetate is dodecyl 2-(N,N-dimethylamino) propionate.

11. The composition in accordance with claim 1 wherein the alkyl N,N-disubstituted-amino acetate is dodecyl 2-(N,N-dimethylamino) propionate hydrochloride.

12. The composition in accordance with claim 1 wherein the small molecule therapeutic is a taxane and the alkyl N,N-disubstituted amino acetate is dodecyl 2-(N,N-dimethylamino) propionate.

13. The composition in accordance with claim 1 wherein the small molecule therapeutic is a taxane and the alkyl N,N-disubstituted amino acetate is dodecyl 2-(N,N-dimethylamino) propionate hydrochloride.

14. The composition in accordance with claim 1 wherein the small molecule therapeutic is paclitaxel and the alkyl N,N-disubstituted amino acetate is dodecyl 2-(N,N-dimethylamino) propionate.

15. The composition in accordance with claim 1 wherein the small molecule therapeutic is a paclitaxel and the alkyl N,N-disubstituted amino acetate is dodecyl 2-(N,N-dimethylamino) propionate hydrochloride.

16. An oral or subcutaneously injectable composition consisting of a taxane, an alkyl N,N-disubstituted-amino acetate, and one or more pharmaceutically acceptable carriers.

17. The composition in accordance with claim 16 wherein the taxane is a member of the group consisting of paclitaxel, docetaxel, tesetaxel, and mixtures thereof.

18. The composition in accordance with claim 16 wherein the alkyl N,N-disubstituted amino acetate is dodecyl 2-(N,N-dimethylamino) propionate.

19. The composition in accordance with claim 16 wherein the alkyl N,N-disubstituted-amino acetate is dodecyl 2-(N,N-dimethylamino) propionate hydrochloride.

20. The composition in accordance with claim 16 wherein the taxane is paclitaxel and the alkyl N,N-disubstituted-amino acetate is dodecyl 2-(N,N-dimethylamino) propionate.

21. The composition in accordance with claim 16 wherein the taxane is paclitaxel and the alkyl N,N-disubstituted-amino acetate is dodecyl 2-(N,N-dimethylamino) propionate hydrochloride.

22. The composition in accordance with claim 4 wherein the alkyl N,N-disubstituted-amino acetate is dodecyl 2-(N,N-dimethylamino) propionate.

23. The composition in accordance with claim 5 wherein the alkyl N,N-disubstituted-amino acetate is dodecyl 2-(N,N-dimethylamino) propionate.

24. The composition in accordance with claim 6 wherein the alkyl N,N-disubstituted-amino acetate is dodecyl 2-(N,N-dimethylamino) propionate hydrochloride.

25. The composition in accordance with claim 7 wherein the alkyl N,N-disubstituted-amino acetate is dodecyl 2-(N,N-dimethylamino) propionate.

26. The composition in accordance with claim 8 wherein the alkyl N,N-disubstituted-amino acetate is dodecyl 2-(N,N-dimethylamino) propionate hydrochloride.

27. The composition in accordance with claim 7 wherein the alkyl N,N-disubstituted-amino acetate is dodecyl 2-(N,N-dimethylamino) propionate hydrochloride.

28. The composition in accordance with claim 9 wherein the alkyl N,N-disubstituted-amino acetate is dodecyl 2-(N,N-dimethylamino) propionate.

29. The composition in accordance with claim 9 wherein the alkyl N,N-disubstituted-amino acetate is dodecyl 2-(N,N-dimethylamino) propionate hydrochloride.

* * * * *